US009649511B2

(12) United States Patent
Nonogaki

(10) Patent No.: US 9,649,511 B2
(45) Date of Patent: May 16, 2017

(54) METHOD OF IRRADIATING SUPERSONIC WAVES

(76) Inventor: Katsunori Nonogaki, Miyagi (JP)

(*) Notice: Subject to any disclaimer, the term of this patent is extended or adjusted under 35 U.S.C. 154(b) by 229 days.

(21) Appl. No.: 14/008,987

(22) PCT Filed: Mar. 31, 2011

(86) PCT No.: PCT/JP2011/058308
§ 371 (c)(1),
(2), (4) Date: Feb. 10, 2014

(87) PCT Pub. No.: WO2012/132001
PCT Pub. Date: Oct. 4, 2012

(65) Prior Publication Data
US 2014/0155789 A1 Jun. 5, 2014

(51) Int. Cl.
A61N 7/00 (2006.01)
A61B 8/00 (2006.01)

(52) U.S. Cl.
CPC ............. A61N 7/00 (2013.01); A61B 8/00 (2013.01); A61N 2007/0013 (2013.01)

(58) Field of Classification Search
CPC .............................. A61N 2007/0078
See application file for complete search history.

(56) References Cited

U.S. PATENT DOCUMENTS 4,883,045 A * 11/1989 Theisz ................. 601/3
4,926,874 A * 5/1990 Lee ................. 600/495
5,620,409 A * 4/1997 Venuto ............ A61B 17/22004 601/2
5,703,922 A * 12/1997 Rattner ................. 378/65
7,429,249 B1 * 9/2008 Winder et al. ............. 601/2
2002/0055693 A1 * 5/2002 Thompson ............ A61N 7/00 601/2
2003/0153849 A1 * 8/2003 Huckle et al. .............. 601/2
2004/0044298 A1 * 3/2004 Kawabata et al. ............... 601/2
2005/0054958 A1 * 3/2005 Hoffmann ............ A61B 17/225 601/46
2007/0038098 A1 * 2/2007 Harris ................. A61N 7/00 600/439
2007/0219481 A1 * 9/2007 Babaev ............... A61M 11/005 604/22

(Continued)

FOREIGN PATENT DOCUMENTS

JP 2000-225161 A 8/2000
JP 2003-526403 A 9/2003

(Continued)

Primary Examiner — Serkan Akar
(74) Attorney, Agent, or Firm — Muncy, Geissler, Olds & Lowe, P.C.

(57) ABSTRACT

An ultrasonic irradiation device 10 includes: an ultrasonic irradiation pad 110 including at least two output elements for emitting supersonic waves with output strength in a range of 50±5 mW/cm$^2$ to 110±5 mW/cm$^2$ at output frequency in a range of 500±50 kHz to 800±50 kHz; drive control device 11 that drivingly controls the ultrasonic irradiation pad 110; and fastening device 120 that fastens the ultrasonic irradiation pad 110 in a state of being in close contact with a forearm 50 of the living body, in which the fastening device 120 is formed into a deformable strip having a removable fixed portion 120a in an end portion.

6 Claims, 8 Drawing Sheets

(56) References Cited

U.S. PATENT DOCUMENTS

2008/0045882 A1* 2/2008 Finsterwald .................... 604/22
2008/0208084 A1* 8/2008 Horzewski ............... H04N 1/58
  601/2
2008/0255049 A1* 10/2008 Sumner ................... A61N 7/00
  514/6.9

FOREIGN PATENT DOCUMENTS

| JP | 2004-81645 | 3/2004 |
| JP | 2004-154304 | 6/2004 |
| JP | 2008-173370 | 7/2005 |

* cited by examiner

METHOD OF IRRADIATING SUPERSONIC WAVES

TECHNICAL FIELD

The present invention is an ultrasonic irradiation device that induces systemic effects by locally irradiating a living body (a human subject, referred to hereafter as the subject) with supersonic waves.

BACKGROUND ART

Conventional medical ultrasound devices that use ultrasonic irradiation induce local effects by irradiating a part of the subject with ultrasonic waves.

This type of medical ultrasound device is currently used for treating bone fractures (refer to patent document 1).

The present device induces systemic effects, including analgesic and anti-inflammatory effects, of not only the irradiated body part, but other parts of the body as well, by regulating blood flow, vascular endothelial function, blood pressure, heart rate, blood glucose, atherosclerosis, sleep, and the autonomic nervous system activity, etc.

The present invention differs from devices that can improve systemic blood flow in subjects by producing micronanobubbles in bathtub water. A gas-liquid mixing circulating pump device generates liquid containing microbubbles or a micronanobubbles, which contribute to improve systemic blood flow.

The device is equipped with a gas shearing piece that shears the gas and generates microbubbles or micro-nanobubbles, and a third compartment that releases the liquid containing micronanobubbles into a bathtub, in which the subject is seated (refer to patent document 2).

[Patent Document1] Provisional-publication-of-a-patent 2004 No. 154304 official report

[Patent Document2] Provisional-publication-of-a-patent 2008 No. 173370 official report

DISCLOSURE OF THE INVENTION

Problems to be Solved by the Invention

The ultrasonic irradiation devices described in patent documents 1 or 2 do not exert systemic effects. In addition, ultrasonic waves with an output frequency greater than 1 MHz and an output intensity of 2 W/cm$^2$ are not available for continuous fixed irradiation to the same region of the subject's body, because of adverse effects such as periosteal pain. Subjects cannot operate the ultrasonic device by themselves, because the device must be moved manually to a region on the subject's body to irradiate the ultrasonic waves approximately every 5 minutes.

In addition, the device described in patent document 2 requires a bathtub in which the subjects can sit and a plumbing device for the liquid containing micro-nanobubbles, thus the positioning of the subject in a bathtub to use the device is limiting and subjects must also be unclothed and immersed in water.

The aims of the present invention are to provide easy access to systemic effects by local irradiation of a subject with ultrasonic waves using an output frequency of 800 kHz or less with low intensity on a forearm (from the elbow to fingers) with a device that can be easily applied by oneself.

Means for Solving the Problems

An ultrasonic irradiation device that generates systemic effects by locally irradiating a subject with supersonic waves comprising: an ultrasound irradiation pad in close contact with the forearm of the subject; an ultrasonic irradiation pad that includes at least two output elements for emitting ultrasonic waves with an output strength ranging from 50±5 mW/cm$^2$ to 110±5 mW/cm$^2$ and an output frequency ranging from 500±50 kHz to 800±50 kHz; a drive control for controlling the ultrasonic irradiation pad; and a fastener, which is a deformable strip having a fixed end and a loose end, that secures the ultrasonic irradiation pad in close contact with the subject's forearm.

Diabetes is a metabolic disease characterized by hyperglycemia associated with vascular complications that shorten the lifespan. Vascular complications include microvascular complications (neuropathy, retinopathy, and nephropathy) and major vascular complications (myocardial infarction and cerebral infarction). Microvascular complications are related to glycemic control (HbA1c), whereas major vascular complications are not directly related to glycemic control. Postprandial hyperglycemia is related to major vascular events and mortality. Improved glycemic control and the prevention of vascular complications are therefore important in the treatment of diabetes.

The ultrasonic irradiation device of the present invention (1) improves systemic vascular disturbances, especially diabetic vascular complications, by irradiating the subject's forearm with ultrasonic waves at an output strength ranging from 50±5 to 110±5 mW/cm$^2$ and an output frequency ranging from 500±50-kHz to 800±50 kHz. More specifically, the ultrasonic irradiation device improves vascular endothelial dysfunction, which is related to ischemic heart disease. Therefore, the ultrasonic irradiation device of the present invention can also be applied clinically to prevent and/or treat vascular diseases, including atherosclerosis.

Type 2 diabetes is often associated with being overweight, which leads to an increased risk for atherosclerosis and ischemic heart disease. Special diets, such as a formula diet (a diet containing high protein, low carbohydrates, low fat, multivitamins, minerals, and high dietary fiber with a low calorie content), may be prescribed for overweight and obese subjects as supportive diet therapy. We have found, however, that body weight reduction by a formula diet does not improve vascular endothelial dysfunction. The ultrasonic irradiation device of the present invention and the ingestion of a formula diet to reduce weight have additive effects for treating obesity and type 2 diabetes associated with vascular complications. In addition, the ultrasonic irradiation device of the present invention induces relaxation and sleep.

Clinical application as an apparatus to induce sleep is therefore also expected.

Because the ultrasonic irradiation device (1) has an ultrasonic irradiation pad that irradiates ultrasonic waves directly in a subject, no liquid or equipment, such as a bathtub, is needed. Moreover, as the ultrasound is irradiated with an ultrasonic irradiation pad at an output frequency ranging from 500±50-kHz to 800±50 kHz and an output intensity ranging from 50±5 mW/cm$^2$ to 110±5 mW/cm$^2$, the drive control that controls the ultrasonic irradiation pad can be compact in size.

Furthermore, the ultrasonic irradiation device (1) is embedded in a band that can be wrapped around the subject's forearm and fixed in place. The fastener band contains the ultrasonic irradiation device in the middle, allowing the two free ends to be coupled in such a way as to fit various sized forearms. The subject irradiates their forearm with an ultrasonic wave by placing the ultrasonic irradiation pad on their forearm using their other hand, and by wrapping the fastener band around their forearm with the other hand by fixing the end of the fastener in a position that places the ultrasonic irradiation pad in direct contact with the subject's forearm.

Accordingly, the ultrasonic irradiation device (1) is easy to install and systemic effects can be obtained by locally irradiating the subject with an ultrasonic wave from the elbow to the wrist at an output frequency of 800±50 kHz or less and a weak output intensity. The ultrasonic irradiation device irradiates the affected part with an ultrasonic wave.

(2) The ultrasonic irradiation device (1) has a drive control for the ultrasonic irradiation pad that can be set to continuously emit supersonic waves. The ultrasonic irradiation device (2), provides greater systemic effects.

(3) The ultrasonic irradiation device (1) has an ultrasonic irradiation pad that emits ultrasonic waves at an output frequency ranging from 500±50 kHz.

Use of the ultrasonic irradiation device (3) can decrease postprandial hyperglycemia by irradiating ultrasonic waves in a subject at an output frequency ranging from 500±50 kHz. For example, diabetic subjects under treatment with anti-diabetic agents (at least one of the following oral hypoglycemic agents: biguanide, thiazolidine derivative, alpha-glucosidase inhibitors, dipeptidyl peptidase 4 inhibitors, sibutramine, and an appetite suppressant or insulin secretagogues, and glucagon-like peptide 1 receptor agonists) exhibited decreased blood glucose levels after irradiation with ultrasonic waves at an output frequency ranging from 500±50 kHz compared with placebo controls.

(4) The ultrasonic irradiation device (1) has an ultrasonic irradiation pad that emits ultrasonic waves with an output frequency ranging from 800±50 kHz.

The ultrasonic irradiation device (4) improves vascular diseases by irradiating the subject with ultrasonic waves at an output frequency in the range of 800±50 kHz. The ultrasonic irradiation device of the present invention, therefore, is available for the prevention and/or treatment of vascular diseases, such as atherosclerosis and ischemic heart diseases.

(5) For ultrasonic irradiation devices (1) through (4), the drive control can be used to control the duration of the ultrasonic irradiation between 20 and 30 minutes.

Use of the ultrasonic irradiation device (5), in which an ultrasonic irradiation pad is in close contact with the subject's forearm, to irradiate the forearm for 20 to 30 minutes improves vascular diseases and enhances the effects of anti-diabetic agents. Because the ultrasonic irradiation pad does not need to be in close contact with the subject's entire body, it is not necessary to force the subject to adopt a posture that the subject cannot maintain.

(6) The ultrasonic irradiation system comprises any one of ultrasonic irradiation devices (1) through (5) and also includes: An installation portion for installing the ultrasonic irradiation device and a chair portion connected to the installation portion. The subject sits in the chair portion, which includes a seat on which the subject is seated; a backrest that is pivotally connected to the seat and allows the subject to lean back; and an armrest connected to the seat that contains the ultrasonic irradiation pad unit.

The ultrasonic irradiation system (6) can be installed next to a seat connected to the backrest that can rotate into a reclining position. That is, the ultrasonic generator can be installed in a chair equipped with a reclining function.

Therefore, the subject can sit on this chair and receive ultrasonic wave irradiation while sitting in a comfortable position. For example, some subjects have difficulty maintaining the same posture even for as little as 10 minutes. Moreover, if the subject must lie supine to receive irradiation, the space required for the irradiation procedure is much larger than that if the subject can be seated in a chair. In a chair equipped with a reclining function, however, the subject can be positioned comfortably while receiving ultrasonic wave irradiation. Accordingly, the ultrasonic irradiation device can be installed in the waiting room of a medical institution.

Effects of the Invention

The present invention can be easily installed to obtain the systemic effects provided by locally irradiating the subject's forearm with ultrasonic waves at an output frequency of 800±50 kHz or less and weak output intensity. Subjects can operate the ultrasonic irradiation device by themselves.

EXPLANATION OF REFERENCE NUMERALS

10 ultrasonic irradiation device
11 drive control
110 ultrasonic irradiation pad

PREFERRED MODE FOR CARRYING OUT THE INVENTION

The enforcement form of the present invention is explained in detail based on the Figures as follows:

In the explanation of the following enforcement forms, the labels for the same composition factors are the same and the explanation is omitted or simplified for identical configurations.

[Composition of the Ultrasonic Irradiation System 1]

Figure 1:
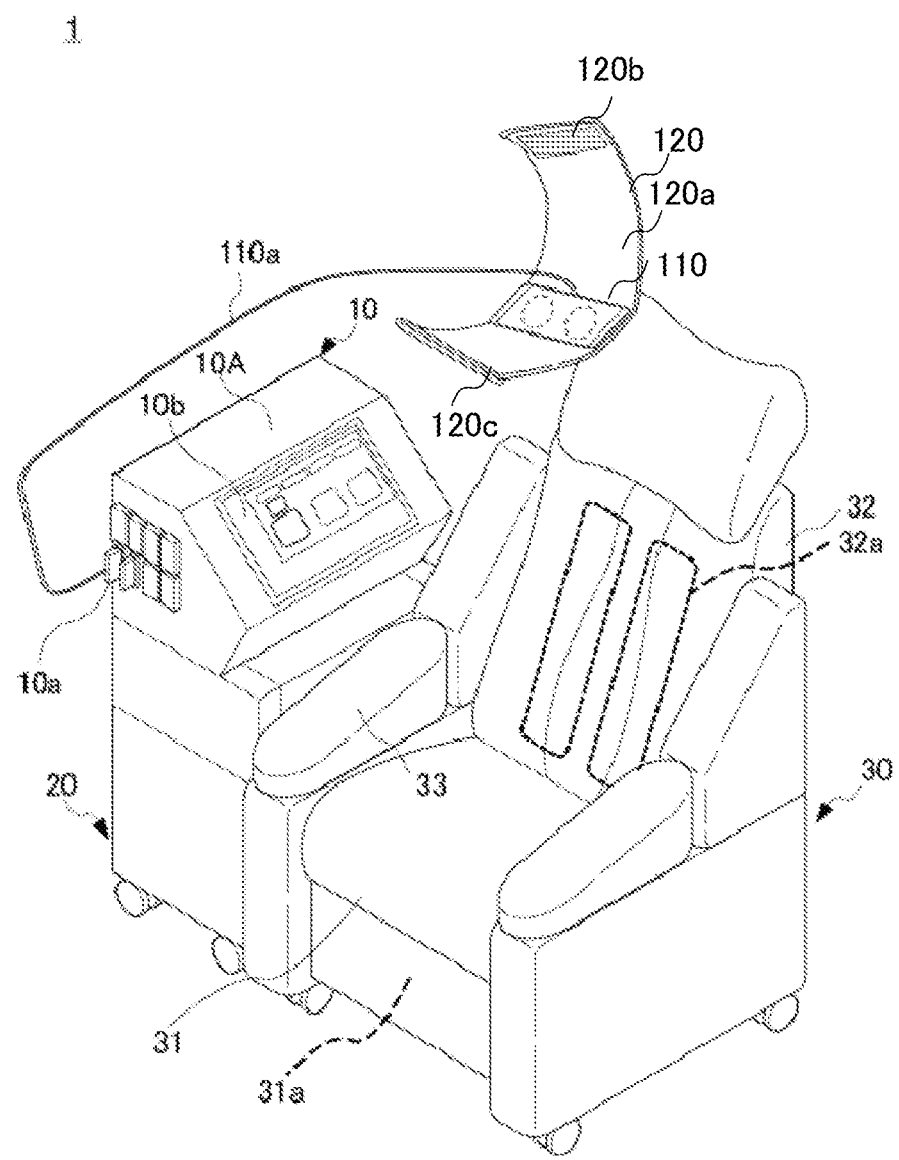
FIG. 1 is a drawing of the entire ultrasonic irradiation system comprising the enforcement form of the present invention.

FIG. 1 depicts the whole ultrasonic irradiation system 1 comprising the enforcement form concerning the present invention.

The ultrasonic irradiation system (1) includes ultrasonic irradiation device 10, which irradiates the subject with ultrasonic waves, installation part 20 on which the ultrasonic irradiation device 10 is installed, and chair part 30 on which the subject sits.

The ultrasonic irradiation device 10 includes the main part 10A, which contains the distribution power board 10b, the ultrasonic irradiation pad 110 connected to the connector 10a of the main part 10A through the composite cable 110a, and the fastener pad 120 as a fastener, which contains the ultrasonic irradiation pad, for fixing the ultrasonic irradiation pad to the subject's forearm.

Installation part 20 is connected to the side of the chair part 30 that can attach and detach, and has four wheels at the lowermost part, which allows the chair part to move.

The chair part 30 includes the seat part 31 on which the subject sits; the backrest part 32, which is connected to the seat part 31 and can rotate, allowing the subject to recline; and the arm rest 33, which is connected to the seat part 31 and connects to the ultrasonic irradiation pad 110. The chair part 30 includes a reclining function.

The backrest part 32 has the roller part 32a, which moves up and down the length of the backrest part, touching the back of the subject. Moreover, the roller control device 31a, which controls operation of the roller part 32a, is contained inside the seat part 31. Thus, chair part 30 includes a massage function.

The details regarding the main part 10A of the ultrasonic irradiation device 10 are described later in FIG. 6.

[Composition of the Ultrasonic Irradiation Pad 110]

Figure 2:
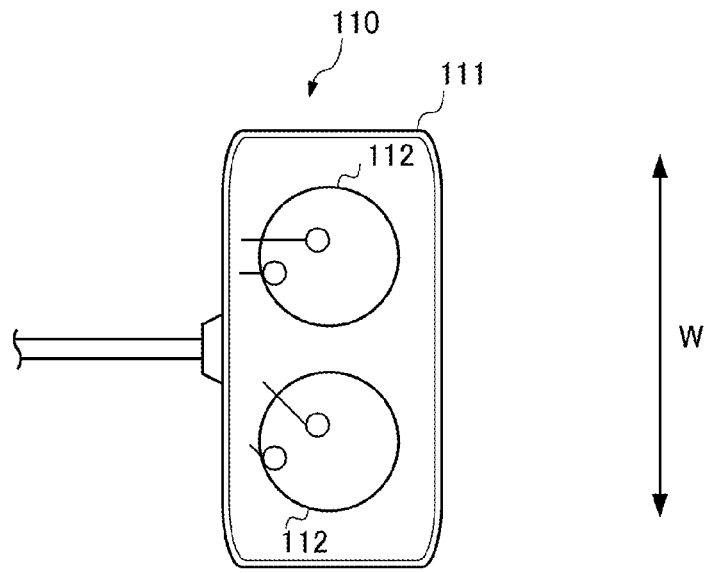
FIG. 2 is a drawing of the composition of an ultrasonic irradiation pad equipped with two ultrasonic oscillation elements for use in the system shown in FIG. 1.

FIG. 2 shows the composition of the ultrasonic irradiation pad 110 that includes two ultrasonic oscillation elements in the above-mentioned enforcement form.

Figure 3:
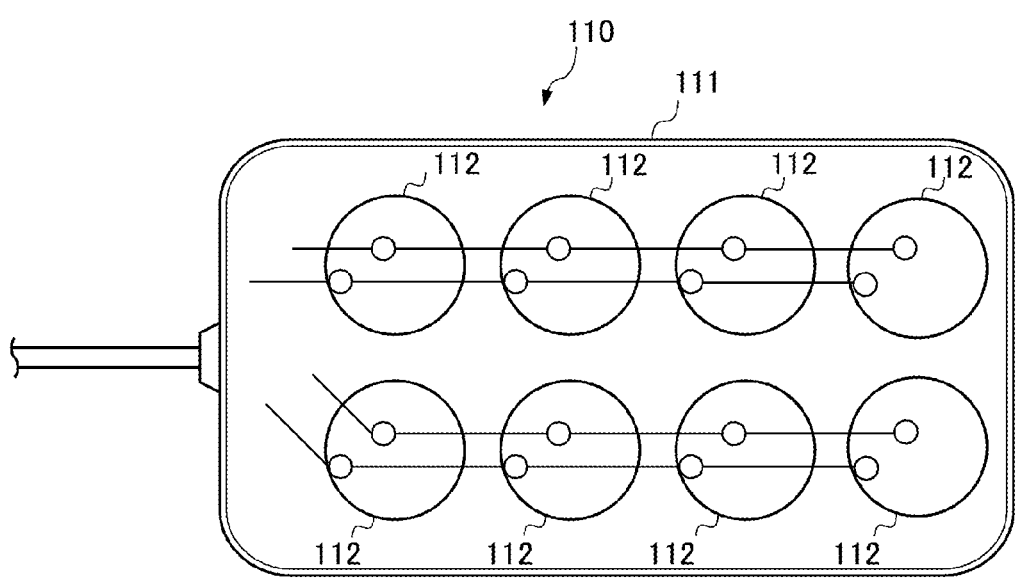
FIG. 3 is a drawing of an ultrasonic irradiation pad equipped with eight ultrasonic oscillation elements for use in the system shown in FIG. 1.

FIG. 3 shows the composition of the ultrasonic irradiation pad 110 that includes eight ultrasonic oscillation elements in the above-mentioned enforcement form. The ultrasonic irradiation pad 110 includes the main part 111 of the pad, which is a bag-like object approximately shaped like a rectangle of sufficient length to wrap around a part of the subject, and ultrasonic oscillation element 112, which are embedded in the main part of the pad 111, and generates an ultrasonic wave.

The upper surface is formed with silicone rubber and, as for the main part 111 of a pad, the undersurface that touches the skin of the subject is formed by conductive silicon rubber.

In addition, the number of the ultrasonic oscillation elements 112 is not limited to two or eight pieces. For example, the number of the ultrasonic oscillation elements 112 can be 4, 6, or 12.

The sizes of the main part 111 of a pad depends on the number of ultrasonic oscillation elements 112. That is, the size of a pad 111 (S size) with 8 ultrasonic oscillation elements 112 is smaller than the size of a pad 111 (L size) with 12 ultrasonic oscillation elements 112.

The ultrasonic oscillation element 112 is arranged so that an ultrasonic wave may be generated from the undersurface of the main part 111 of a pad.

Drive control of the ultrasonic oscillation element 112 is carried out by the drive control chip 11 described below. Although described later in detail, the ultrasonic irradiation device 10 of this enforcement form can generate ultrasonic waves with four output frequencies.

The ultrasonic irradiation pad 110 of this enforcement form has eight variations; the above-mentioned four different output frequencies and the above-mentioned two different types of pads 111.

Returning to FIG. 1, the fastener pad 120 includes a flexible strip 120a, a fastener portion 120b that is placed at one end of strip 120a, a fixing portion that can attach to the fastener 120b and is placed at a predetermined position on strip 120a, and a loosely inserted ring 120c that is placed at the end of the strip 120a opposite that of 120b.

The fixing portion on 120a comprises a set of hooks or the like, and the fastener portion 120b comprises a set of loops or the like.

Figure 4:
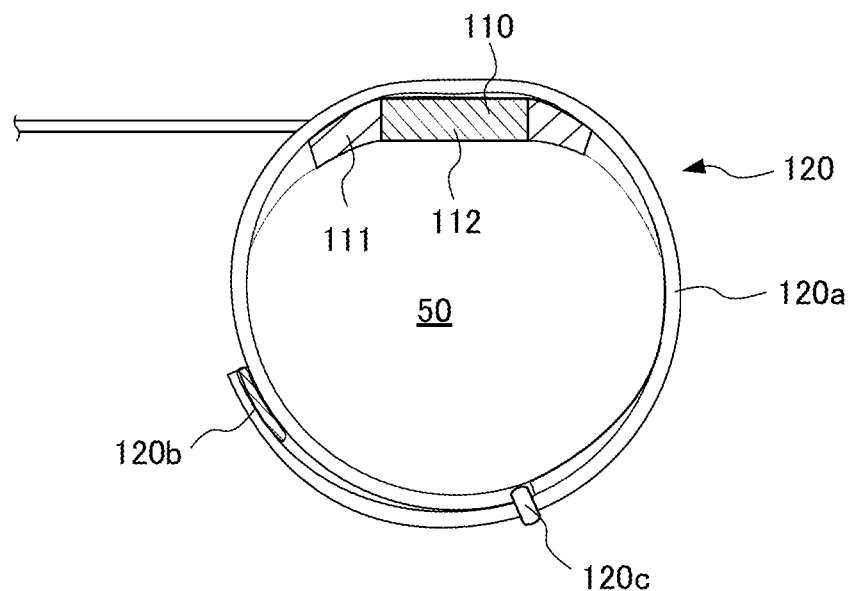
FIG. 4 is a diagram of the ultrasonic irradiation pad of the above-mentioned enforcement form, and a fastener pad.

FIG. 4 is a diagram of the ultrasonic irradiation pad 110 in the above-mentioned enforcement form, and the fastener pad 120.

With this enforcement form, the ultrasonic oscillation element 112 uses two ultrasonic irradiation pads 110.

As shown in FIG. 4, the ultrasonic irradiation pad 110 is arranged such that the array direction (the direction of W in FIG. 2) of the ultrasonic oscillation elements 112 placed against the forearm 50 in the direction from the elbow of the subject toward the palm.

The fastener pad 120 is in the state where the ultrasonic irradiation pad 110 was made to touch the forearm 50 of the subject, it wraps the band 120a around the forearm 50, passes the band 120a through the ring 120c, and fixes the holding part 120b to the suitable position of the band form 120a.

In this enforcement form, the forearm 50 includes a peripheral part from the elbow of the subject. The ultrasonic irradiation pad 110 is made to directly touch the forearm 50 of the subject, and is fixed to the forearm 50 with the fastener pad 120.

The suitable position in this enforcement form is a position that does not press the forearm 50 and attaches, and is easy to detach the holding part 120b using a single hand. To easily attach and detach the fastener pad 120 with one hand, when the forearm 50 is the left arm, and the holding part 120b is attached with the right hand, for example, it is desirable to have the holding part 120b on the right-hand side.

Figure 5:
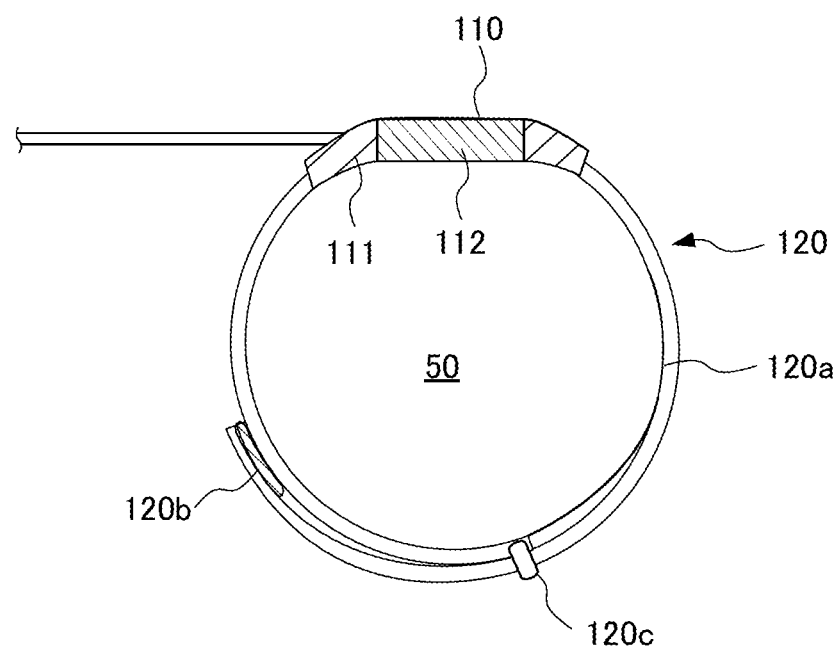
FIG. 5 is a diagram of the ultrasonic irradiation pad of modification (1), shown in the fixed position, for use in the system shown in FIG. 1.

FIG. 5 is a diagram of modification 1 of the ultrasonic irradiation pad 110 and the fastener pad 120 of the above-mentioned enforcement form.

Modification (1) differs from the above-mentioned enforcement form in that the ultrasonic irradiation pad 110 and the fastener pad 120 are integrated as a single unit.

Figure 6:
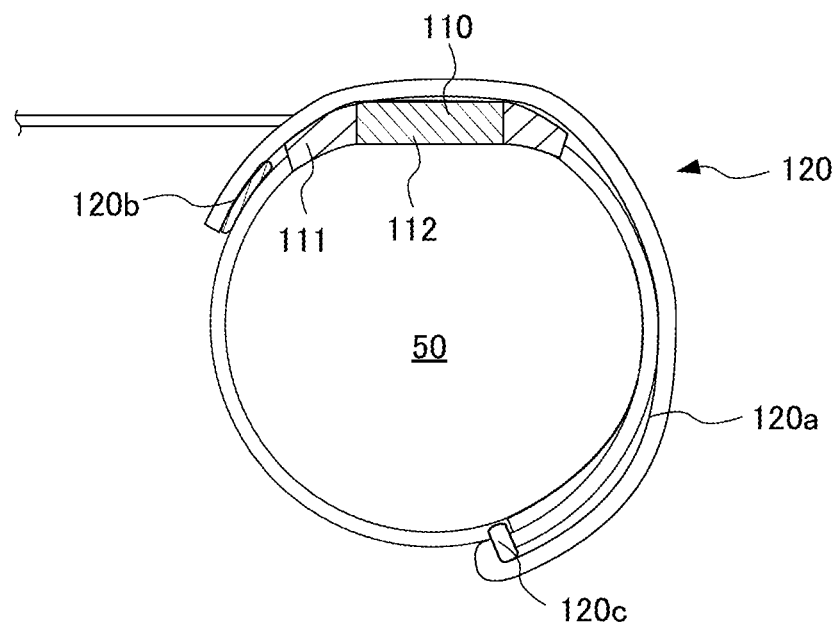
FIG. 6 is a diagram of the ultrasonic irradiation pad of modification (2), shown in the fixed position, for use in the system shown in FIG. 1.

FIG. 6 is a diagram of modification (2) of the ultrasonic irradiation pad 110 and the fastener pad 120 of the above-mentioned enforcement form.

Modification (2) includes the fastener pad 120, after passing one end of the band form 120a through the ring 120c the band form 120a turns 180 degrees, and the fastener part 120b is fixed to the suitable position of the band form 120a. This is a different from modification (1). The user can therefore fix the fastener part 120b to the suitable position of the band form 120a when the user's arm is thin.

Figure 7:
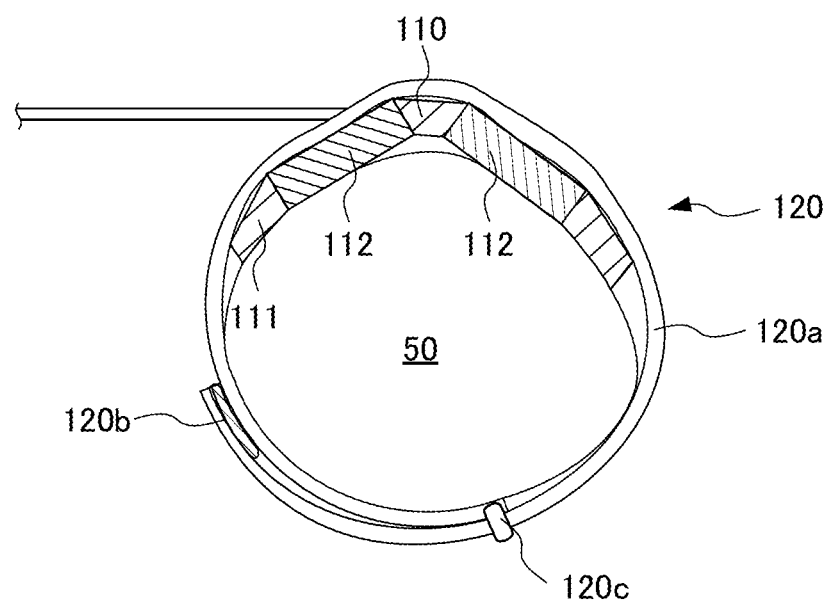
FIG. 7 is a diagram of the ultrasonic irradiation pad of modification (3), shown in the fixed position, for use in the system shown in FIG. 1.

FIG. 7 is a diagram modification (3) of the ultrasonic irradiation pad 110 and the fastener pad 120 of the above-mentioned enforcement form.

Modification (3) is arranged such that the ultrasonic irradiation pad 110 touches the forearm 50 with the array direction (the direction of W in FIG. 2) of the ultrasonic oscillation element 112 perpendicular to the direction from the elbow to the palm.

[Functional Composition of the Ultrasonic Irradiation Device 10]

Figure 8:
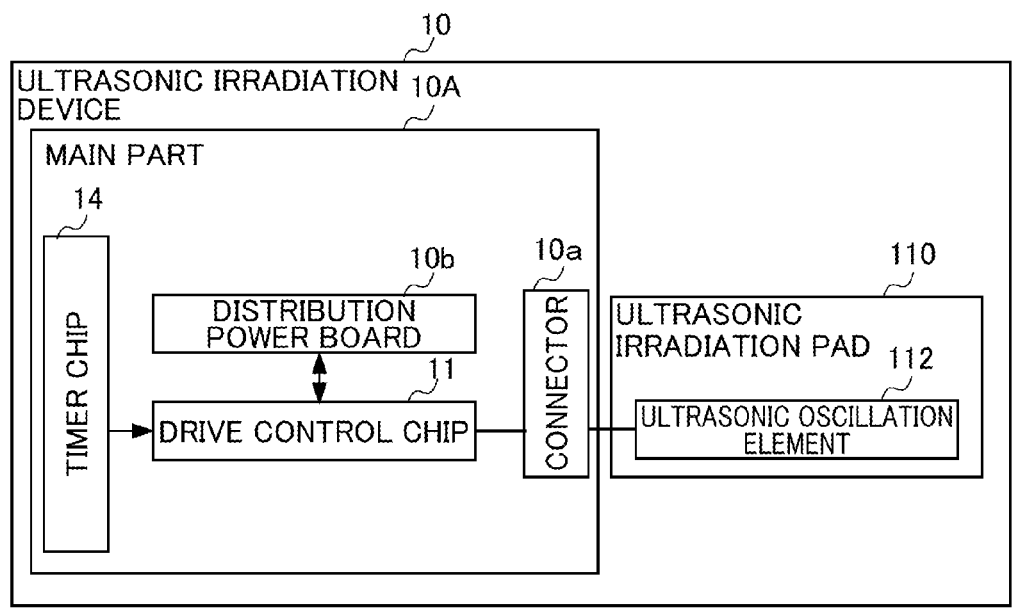
FIG. 8 shows the functional composition of the ultrasonic irradiation device of the system shown in FIG. 1.

FIG. 8 is a schematic showing the functional composition of the ultrasonic irradiation device 10 of the above-mentioned enforcement form.

The ultrasonic irradiation device 10 includes the main part 10A and the ultrasonic irradiation pad 110, which is connected via connector 10a of the main part 10A and the ultrasonic oscillation element 112.

The main part 10A includes a drive control chip 11, which controls the ultrasonic oscillation element 112, and a timer chip 14, which transmits time information to the drive control chip 11.

The drive control chip 11 operates the drive control of the ultrasonic oscillation element 112 to continuously irradiate the ultrasonic waves at a specific output frequency and output intensity.

The output intensity in this enforcement form ranges from 50 to 110 $mW/cm^2$. As the output intensity of the present invention varies, the range includes the standard error of the mean (SEM) such that the actual range is (mean±SEM) 50±5 to 110±5 $mW/cm^2$.

The output frequency in this enforcement form includes 4 frequencies (mean±SEM); placebo irradiation (0 kHz), 500±5 kHz, 800±5 kHz, and 1000±5 kHz. According to the input operation from the distribution power board 10b, the drive control chip 11 changes these four output frequencies and carries out drive control of the ultrasonic oscillation element 112.

In this enforcement form, although output frequency is set to 500±5 kHz and 800±5 kHz, the present invention has an output frequency ranging from 500±50 kHz to 800±50 kHz, including standard errors.

Moreover, the drive control chip 11 operates the drive control to continuously irradiate the ultrasonic wave for a preset period of time (e.g., 30 minutes), with the timing set beforehand based on the time information transmitted from the timer chip 14 and it starts the drive control of the ultrasonic oscillation element 112.

The timer chip 14 counts time and transmits time information to the drive control chip 11 according to the input operation from the distribution power board 10b.

The timer chip 14 can be set from 0 through 30 minutes, and the timing signal, which transmits time information per minute, is received by the drive control chip 11.

Moreover, the timer chip 14 can generate a sound (not illustrated) to provide a sound at set intervals.

The connector 10a allows for a total of eight combinations of the four above-mentioned output frequencies, and the two above-mentioned pads 111 (FIG. 1).

The distribution power board 10b sends various inputs to the ultrasonic irradiation device 10 depending on the operator-controlled setting.

The drive control chip 11 in the ultrasonic irradiation device 10 and the timer chip 14 comprises the computer and hardware, which is comprised by software.

The above-mentioned hardware comprises a central processing unit (CPU), as the drive control chip 11 and the timer chip 14, and storage devices. The storage devices include memory (random access memory [RAM] and read only memory [ROM]), hard disk drives (HDD), and optical disc drives (compact disk [CD], digital versatile disk [DVD], etc.). In addition, the ultrasonic irradiation device 10 can be equipped with various displays such as a liquid crystal display, a plasma display, etc. Moreover, the ultrasonic irradiation device 10 can be equipped with a keyboard and pointing devices (e.g., mouse, track ball, etc.) as an input device.

The above-mentioned software includes the computer program and data, which control the above-mentioned hardware. The computer program and data are contained in the storage part, and are suitably performed, and referred to by each control device.

Figure 9:
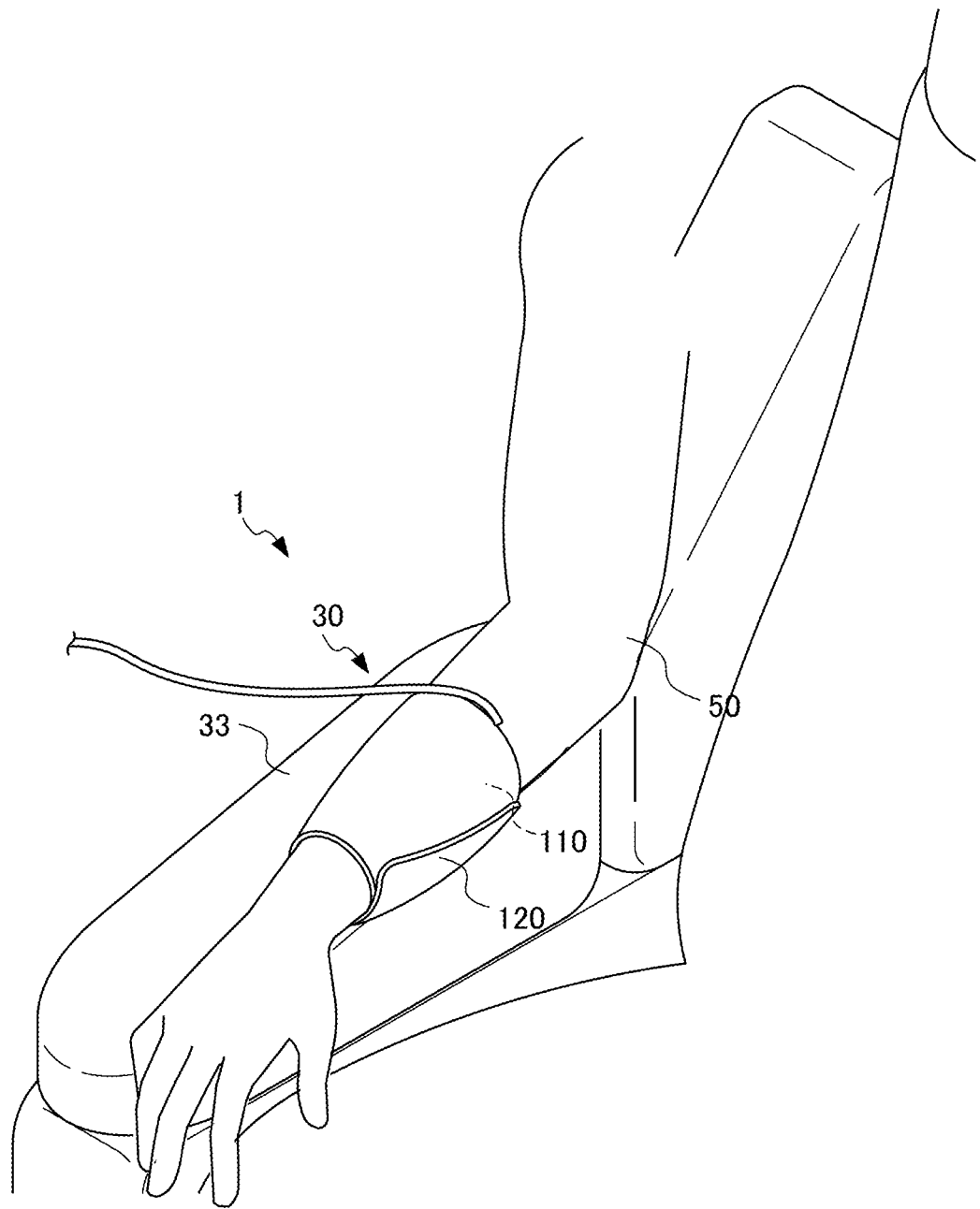
FIG. 9 is a drawing showing the ultrasonic irradiation system shown in FIG. 1 applied to a subject.

FIG. 9 is a drawing in which the ultrasonic irradiation system 1 of the above-mentioned enforcement form is applied to a subject.

With this enforcement form, when applying the ultrasonic irradiation system 1 to a subject, the subject is seated in chair part 30, and places a forearm 50 on the armrest 33 from the elbow down. The ultrasonic irradiation pad 110 of the ultrasonic irradiation equipment 10 is made to come in contact with a part of a subject's forearm 50, and is fixed to the subject's forearm 50 with the fastener pad 120. In this state, a part of the subject's forearm 50 is irradiated with the ultrasonic wave at an output intensity ranging from 50 $mW/cm^2$ to 110 $mW/cm^2$ for up to 30 minutes with an output frequency ranging from 500±5-kHz to 800±5 kHz.

[Case 1, in which the Ultrasonic Irradiation System (1) was Applied to Subjects]

Figure 10:
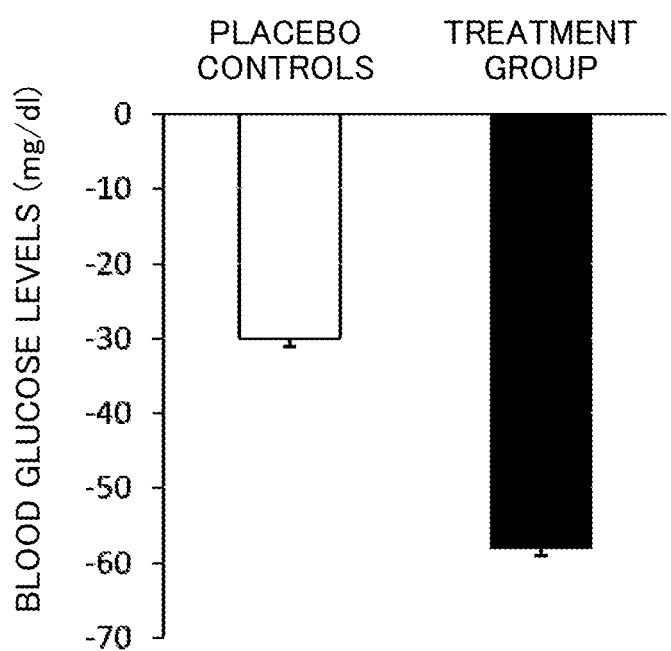
FIG. 10 shows the blood glucose levels after applying the ultrasonic irradiation device to the subjects compared to placebo controls.

FIG. 10 shows Case 1, in which the ultrasonic irradiation system (1) was applied to subjects.

Subjects in Case 1 were diabetic patients prescribed anti-diabetic agents, including insulin secretagogues (sulfonylurea, glinide, and dipeptidyl peptidase 4 inhibitors), thiazolidine derivative oral hypoglycemic agents (pioglitazone), biguanide (metformin), and alpha-glucosidase inhibitors (voglibose), or insulin.

In Case 1, the subjects were both men and women with a mean age of 63 years and a mean HbA1c of 7.0%.

In Case 1, blood glucose levels were measured 2 h after a meal in the irradiation group (8 subjects who were irradiated with ultrasonic waves using the ultrasonic irradiation device 1), and a placebo group (10 subjects who were not irradiated with the ultrasonic waves). Blood glucose levels were measured after irradiating the forearm of the subjects with ultrasonic waves at an output frequency of 500 kHz and an output intensity 50 $mW/cm^2$ for 30 min.

FIG. 10 shows the changes in the blood glucose levels before and after irradiation with ultrasonic waves using the ultrasonic irradiation system (1) in placebo controls (white bar) and irradiated subjects (black bar).

Basal blood glucose levels were not significantly different between controls and those treated with ultrasonic irradiation (controls; 178±7 mg/dl and ultrasonic irradiation group: 182±15 mg/dl). At 30 minutes, the decrease in blood glucose levels was significantly greater in the group treated with ultrasonic irradiation compared with the placebo controls (irradiation, 58±7 mg/dl and controls, 28±5 mg/dl; Student's-t test $P<0.05$).

These findings indicate that ultrasonic irradiation with ultrasonic waves at an output frequency of 500 kHz and an output intensity 50 $mW/cm^2$ for 30 minutes on the forearm of the subjects using device 1 significantly decreased blood glucose levels in diabetic patients taking anti-diabetic agents.

[Case 2, in which Ultrasonic Irradiation System (1) was Applied to Subjects at Various Frequencies]

Figure 11:
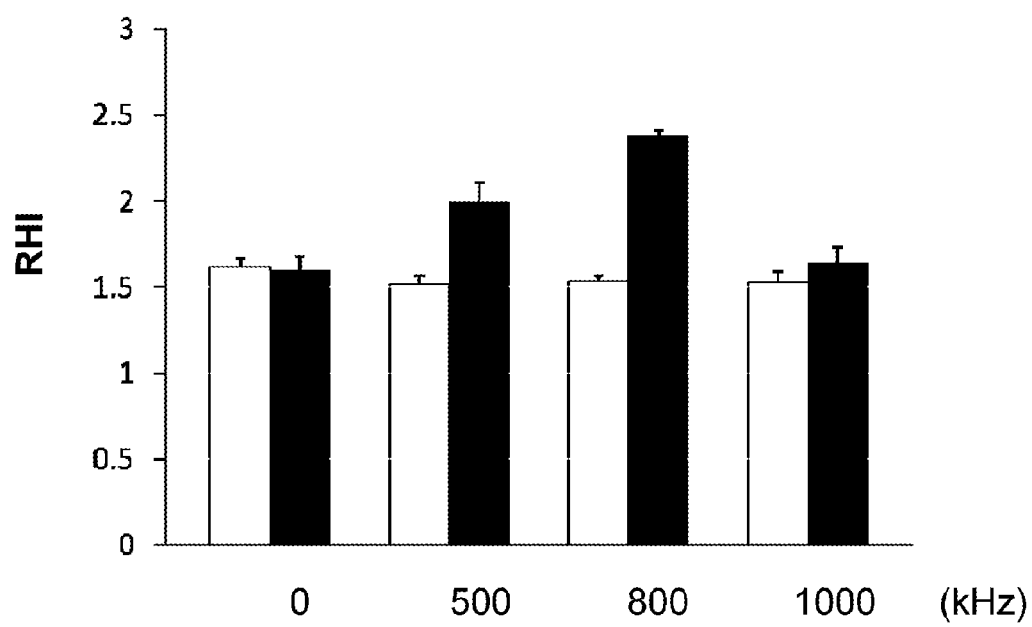
FIG. 11 shows the mean RHI before and after applying the ultrasonic irradiation device to subjects.
Figure 12:
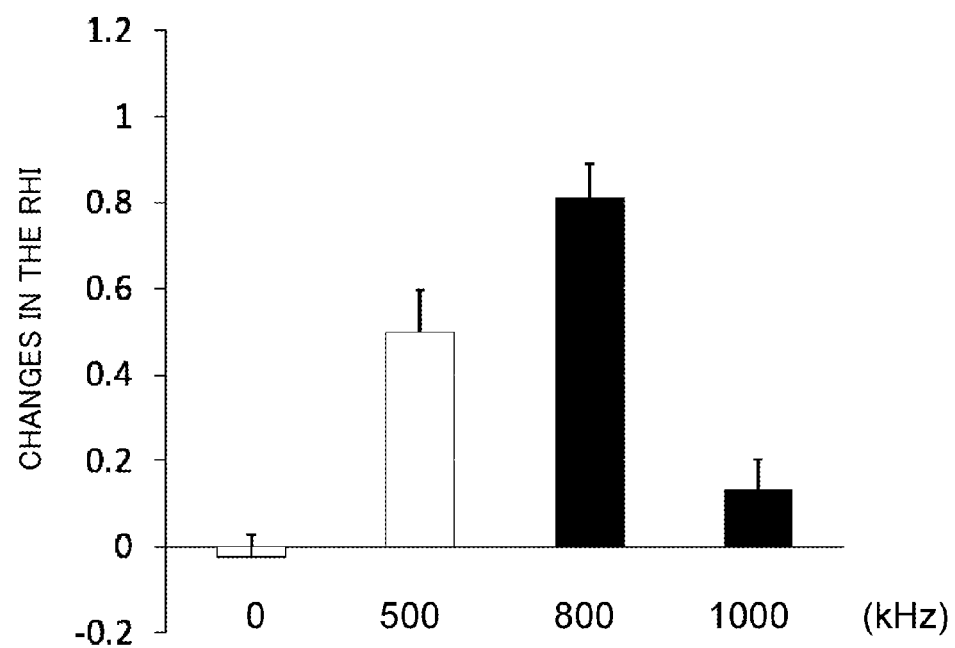
FIG. 12 shows the changes in the mean RHI before and after applying the ultrasonic irradiation device to the subjects.

FIGS. 11 and 12 show Case 2, in which ultrasonic irradiation system (1) was applied to subjects using various frequencies.

Case 2 demonstrates the effect of the ultrasonic irradiation system (1) on the reactive hyperemic index (RHI), which reflects endothelial function. A normal RHI value is >1.67.

Moreover, in Case 2, the effects on RHI of different output frequencies: 0 kHz, 500 kHz, 800 kHz, and 1000 kHz, and ultrasonic waves at an output intensity of 50 mW/cm$^2$ irradiated in the forearm 50 of subjects for 30 minutes were determined before and after treatment with the ultrasonic irradiation system (1) (FIG. 11 and FIG. 12).

FIG. 11 shows the effects of ultrasonic irradiation at different output frequencies on the mean RHI value in subjects before and after ultrasonic irradiation. In FIG. 11, the white bar graph shows the mean RHI value before ultrasonic irradiation. The black bar graph shows the mean RHI value after ultrasonic irradiation. The error bars are the standard error of the mean.

FIG. 12 shows the difference in the mean RHI value between before and after treatment with ultrasonic irradiation shown in FIG. 11. The error bars are the standard error of the mean.

FIGS. 11 and 12 show that the order of efficacy (from greatest to least) to increase RHI of the four frequencies of ultrasonic irradiation examined was 800 kHz, 500 kHz, 1000 kHz, and 0 kHz (ANOVA, P<0.05).

These findings indicate that an output frequency of 800 kHz had the most potent effect on endothelial function in the range of output frequencies from 500 kHz through 1 MHz.

REFERENCE EXAMPLE

In the reference example, at an output frequency of 750 kHz, intermittent irradiation with ultrasonic waves at an output intensity of 60 mW/cm$^2$ was carried out for 30 minutes on a part of the forearm 50 of a 45-year-old subject (Case 3) with obesity and hypertension. The subject's systolic and diastolic blood pressure were measured before and after treatment with the ultrasonic irradiation device comprising one ultrasonic wave oscillation element 112.

Two days later, the same subject's systolic and diastolic blood pressure were measured again before and after another treatment with the ultrasonic irradiation device.

Table 1 shows the measured values of the subject's systolic and diastolic blood pressure.

TABLE 1

|  | First irradiation | | Second irradiation | |
| --- | --- | --- | --- | --- |
|  | Pretreatment | Posttreatment | Pretreatment | Posttreatment |
| Systolic blood pressure (mmHg) | 217 | 208 | 217 | 219 |
| Diastolic blood pressure (mmHg) | 137 | 138 | 139 | 139 |
| Number of oscillation elements | one element | | one element | |

Second Irradiation: 2 Days after the First Irradiation

Although systolic blood pressure seemed to be slightly decreased after irradiation with one ultrasonic oscillation element generating intermittent irradiation with ultrasonic waves, as shown in Table 1, diastolic blood pressure did not change. Moreover, systolic blood pressure returned to the basal levels within 2 days after the first irradiation treatment, and there was no blood pressure-lowering effect by irradiation. The systolic blood pressure did not decrease after the second ultrasonic irradiation. These results indicate that the use of one ultrasonic oscillation element with an intermittent irradiation at 60 mW/cm$^2$ and an output frequency of 750 kHz has no blood-pressure lowering effect.

[Case 3, in which Ultrasonic Irradiation System (1) with 2 or 12 Oscillation Elements was Applied to a Subject]

For Case 3, we used either 12 or 2 ultrasonic oscillation elements 112 with ultrasonic irradiation system (1). At an output frequency of 800 kHz, continuous irradiation with ultrasonic waves at an output intensity of 50 mW/cm$^2$ was carried out for 30 minutes on a part of forearm 50 of the same subject as in the above-mentioned reference example using 12 ultrasonic oscillation elements 112, and the subject's systolic and diastolic blood pressure were measured before and after each treatment. Two days later, the same subject was irradiated with ultrasonic waves using the same parameters but with only 2 ultrasonic oscillation elements 112, and systolic and diastolic blood pressure were measured.

Table 2 shows the effect of ultrasonic irradiation on blood pressure.

TABLE 2

|  | First irradiation | | Second irradiation | |
| --- | --- | --- | --- | --- |
|  | Pretreatment | Posttreatment | Pretreatment | Posttreatment |
| Systolic blood pressure (mmHg) | 211 | 203 | 199 | 182 |
| Diastolic blood pressure (mmHg) | 151 | 129 | 131 | 125 |
| Number oscillation of elements | 12 elements | | 2 elements | |

Second Irradiation: 2 Days after the First Irradiation

As shown in Table 2, when ultrasonic waves were applied using more than two ultrasonic oscillation elements 112 to continuously irradiate the forearm for 30 minutes, hypertension was improved. In addition, 2 days after the first irradiation treatment, the systolic blood pressure was lower than that before the first treatment.

Moreover, the second irradiation further decreased blood pressure. Thus, irradiation with ultrasonic waves by ultrasonic irradiation device 1 gradually improved hypertension.

These results demonstrate that arrays of 2 and 12 ultrasonic oscillation elements have blood-pressure lowering effects in subjects with hypertension.

[Case 4, in which the Ultrasonic Irradiation System (1) was Applied to a Subject]

In Case 4, ultrasonic irradiation system (1) with two ultrasonic oscillation elements 112 at an output frequency of 800 kHz and an output intensity of 50 mW/cm$^2$ was continuously operated for 30 minutes on the subject's forearm 50, and the subject's blood pressure was measured at 16 minutes and 30 minutes after starting the irradiation.

The subject had hypertension induced by the administration of pain medication for pain in the left hand, shoulder, and neck.

Table 3 shows the subject's blood pressure.

TABLE 3

|  | Pretreatment | 16 min | 30 min |
| --- | --- | --- | --- |
| Systolic blood pressure (mmHg) | 189 | 180 | 169 |
| Diastolic blood pressure (mmHg) | 100 | 99 | 96 |
| Number of oscillation elements | | 2 elements | |

As shown in Table 3, continuous irradiation with ultrasonic waves for 16 minutes or 30 minutes decreased blood pressure in a subject with drug-induced hypertension.

Pain from the left side of the neck to the shoulder disappeared 1 month after the irradiation treatment and the subject required no pain medication after the irradiation treatment.

[Case 5, in which Ultrasonic Irradiation Equipment 1 was Applied to Six Subjects with Hypertension]

In Case 5, a part of the forearm 50 of 6 nondiabetic subjects with hypertension (mean age: 50±5 years old) was irradiated with ultrasonic waves at an output intensity of 50 mW/cm$^2$ and an output frequency of 800 kHz for 30 minutes, and blood pressure and pulse rate were measured before and after treatment with ultrasonic irradiation device 1.

Table 4 shows the effects of the ultrasonic irradiation for 30 minutes on blood pressure and pulse rate in subjects with hypertension (>140 mmHg of systolic blood pressure).

TABLE 4

|  | Pretreatment | Posttreatment |
| --- | --- | --- |
| Systolic blood pressure (mmHg) | 146 ± 8 | 126 ± 6 |
| Diastolic blood pressure (mmHg) | 85 ± 4 | 78 ± 2 |
| pulse rate | 90 ± 7 | 76 ± 3 |

As shown in Table 4, blood pressure and the pulse rate significantly decreased after irradiation in subjects with hypertension (Student's-t test; p<0.05).

[Case 6, in which the Ultrasonic Irradiation System (1) was Applied to Six Subjects with Type 2 Diabetes and Hypertension]

In Case 6, ultrasonic waves with an output frequency of 500 kHz and an output intensity of 50 mW/cm$^2$ were irradiated on the forearm 50 for 30 minutes in 6 subjects (mean age: 65±4 years old) with type 2 diabetes and hypertension. Blood pressure, pulse rate, and blood glucose levels were measured before and after treatment with ultrasonic irradiation system (1).

Table 5 shows the effects of the ultrasonic irradiation on blood pressure, pulse, and blood glucose levels in subjects with type 2 diabetes and hypertension.

TABLE 5

|  | Pretreatment | Posttreatment |
| --- | --- | --- |
| Systolic blood pressure (mmHg) | 150 ± 2 | 134 ± 3 |
| Diastolic blood pressure (mmHg) | 86 ± 3 | 79 ± 2 |
| Pulse rate | 76 ± 3 | 75 ± 2 |
| Blood glucose (mg/dl) | 221 ± 15 | 172 ± 8 |

As shown in Table 5, blood systolic and diastolic pressure, pulse rate, and blood glucose levels were significantly decreased after treatment with the ultrasonic irradiation device 1 for 30 minutes (Student's-t test; p<0.05).

In the above cases, irradiation with ultrasonic waves was confirmed to exert systemic effects in human subjects.

An output frequency of 500 kHz had anti-diabetic effects.

An output frequency of either 500 or 800 kHz led to improvement in vascular endothelial function.

An output frequency of either 500 or 800 kHz had anti-hypertension effects and decreased pulse rate.

An output frequency of either 500 or 800 kHz had systemic analgesic and anti-inflammatory effects.

In addition, an output frequency of either 500 or 800 kHz reduced pain and/or numbness in patients with diabetic neuropathy, chronic pain from the neck to the shoulder in patients with cervical spine symptoms, and lumbago in obese subjects.

Furthermore, irradiation with ultrasonic waves at an output intensity of either 50 mW/cm$^2$ or 110 mW/cm$^2$ and an output frequency of 500 and 800 kHz improved vascular endothelial function, decreased pulse rate, and had anti-hyperglycemic, anti-hypertension, and systemic analgesic and anti-inflammatory effects.

The following action effects are produced with this enforcement form.

According to the ultrasonic irradiation device 10, irradiating the forearm of a subject with ultrasonic waves at an output frequency ranging from 500±50-kHz to 800±50 kHz and an output intensity ranging from 50±5 mW/cm$^2$ to 110±5 mW/cm$^2$ can improve vascular diseases such as atherosclerosis in subjects as a systemic effect, and prevent the vascular complications of diabetes. More specifically, the ultrasonic irradiation device that is the present invention improves vascular endothelial dysfunction, which is related to ischemic heart disease. Thus, the ultrasonic irradiation device has clinical applications as an apparatus to prevent or treat vascular diseases.

In addition, the ultrasonic irradiation from the elbow to the wrist of a subject using the ultrasonic irradiation system 1 plus the ingestion of anti-obesity food to reduce body weight improves vascular endothelial dysfunction.

Moreover, because ultrasonic irradiation induces relaxation, leading to a comfortable sleep, the ultrasonic irradiation device can be applied as a sleep-induction device.

Moreover, because ultrasonic irradiation device 10 allows the ultrasonic irradiation pad 110 to act directly on the subject, no liquid such as water in a bathtub, is required. Moreover, because the ultrasonic irradiation pad 110 includes the drive control chip 11 with an output intensity ranging from 50±5 mW/cm$^2$ to 110±5 mW/cm$^2$ and an output frequency ranging from 500±50-kHz to 800±50 kHz, the drive control chip 11 can be made small.

Moreover, the ultrasonic irradiation device 10 connects to a fastener pad 120 that has a flexible band, which contains fastener part 120a that can be freely detached and attached to the end of the fastener band and can be adapted to fix the ultrasonic irradiation pad 110 around the forearm 50 of the subject. The subject can fix the device 10 to their own forearm 50 by placing the ultrasonic irradiation pad 110 on their forearm 50 using their other hand by holding the end of fastener band 120*a*.

Moreover, because the ultrasonic irradiation device 10 continuously irradiates with ultrasonic waves, it can have larger systemic effects.

Moreover, the ultrasonic irradiation device 10 can decrease blood glucose levels by irradiating the subject with ultrasonic waves at an output frequency ranging from 500±50 kHz. For example, diabetic patients are usually treated with anti-diabetic agents. By irradiating diabetic patients with ultrasonic waves at an output frequency ranging from 500±50 kHz, the effects of the anti-diabetic agents are enhanced and blood glucose levels are decreased.

Moreover, ultrasonic irradiation device 10 irradiates the subject with ultrasonic waves with an output frequency of 800±50 kHz, and can improve vascular diseases. Therefore, the ultrasonic irradiation device of the present invention has clinical application as an apparatus to prevent and/or treat vascular diseases.

Moreover, the ultrasonic irradiation device 10 includes an ultrasonic irradiation pad 110 that contacts the forearm of the diabetic subject and irradiates with an ultrasonic wave for 20 to 30 minutes, thereby improving hyperglycemia and/or vascular complications. Because it is not necessary that the ultrasonic irradiation pad 110 be in contact with the whole body, it is not necessary for patients to maintain an uncomfortable position, such as in a bathtub.

Moreover, ultrasonic irradiation device 10 can be installed as part of a chair 31 so that the backrest part 32 can recline. Thus, the ultrasonic generator 10 can be installed in a chair 30 equipped with a reclining function.

Therefore, diabetic patients can be seated in this chair 30 to receive irradiation with ultrasonic waves while in a comfortable position.

Moreover, in chair part 30 in which the ultrasonic irradiation device 10 is installed, a roller control device 31*a* can move a roller part 32*a*. That is, an ultrasonic generator can be installed in a chair equipped with a massage function.

Therefore, diabetic patients seated in chair part 30 can receive a massage and irradiation with ultrasonic waves that increase systemic blood flow, leading to synergistic effects on the vascular complications of diabetes.

As mentioned above, according to this enforcement form, patients can operate the chair features by themselves because it can be easily installed and the systemic effects can be obtained by locally irradiating with ultrasonic waves from the elbow of the subject to the wrist at an output frequency of 800±50 kHz or less with a weak output intensity.

As mentioned above, although the enforcement form of the present invention was explained, the present invention is not limited to the enforcement form mentioned above. Moreover, only the most suitable effects are described in the enforcement form of the present invention, and the effects of the present invention are not limited to what is described in the enforcement form of the present invention.

The invention claimed is:

1. A method of irradiating supersonic waves for obtaining at least an effect in a subject in need thereof, comprising:
   securing an ultrasonic irradiation pad to a forearm of the subject; and
   irradiating the forearm by oscillation elements,
   obtaining at least one of the effects from the group consisting of anti-hypertension, decreased pulse rate, vascular endothelial function, systemic analgesic, and anti-hyperglycemic effect throughout the body in the subject via regulating blood flow by irradiating the forearm with supersonic waves,
   wherein at least one of the effects of irradiation occurs in a different location than the forearm wherein a drive control means drivingly controls the ultrasonic irradiation pad to emit supersonic waves at 100% duty,
   wherein the ultrasonic irradiation pad emits supersonic waves at a predetermined output intensity and at output frequency in a range of 800±50 kHz, and
   wherein the drive control means controls duration of driving the ultrasonic irradiation pad to continuously emit supersonic waves in a range of 20 to 30 minutes.

2. The method of claim 1, wherein the at least one of the effects is anti-hypertension effect.

3. The method of claim 1, wherein the at least one of the effects is decreased pulse rate.

4. The method of claim 1, wherein the at least one of the effects is improved vascular endothelial function (or reactive hyperemic index).

5. The method of claim 1, wherein the at least one of the effects is systemic analgesic effect.

6. The method of claim 1, wherein the at least one of the effects is anti-hyperglycemic effect.

* * * * *